United States Patent [19]
Gressel et al.

[11] Patent Number: 6,096,686
[45] Date of Patent: Aug. 1, 2000

[54] USE OF GLYPHOSATE SALTS IN SEED DRESSING HERBICIDAL COMPOSITIONS

[75] Inventors: Jonathan Gressel, Rehovot; Daniel M. Joel, Kiryat Tivon, both of Israel

[73] Assignees: Yeda Research and Development Co. Ltd., Rehovot; The State of Israel Ministry of Agricultural, Agriculture Research Organization, Beit Dagan, both of Israel

[21] Appl. No.: 09/101,330
[22] PCT Filed: Jan. 5, 1997
[86] PCT No.: PCT/IL97/00007
§ 371 Date: Dec. 7, 1998
§ 102(e) Date: Dec. 7, 1998
[87] PCT Pub. No.: WO97/24931
PCT Pub. Date: Jul. 17, 1997

[30] Foreign Application Priority Data

Jan. 7, 1996 [IL] Israel ........................................ 116695

[51] Int. Cl.⁷ .................................................. A01N 57/02
[52] U.S. Cl. ........................................... 504/100; 504/206
[58] Field of Search ..................................... 504/206, 100

[56] References Cited

U.S. PATENT DOCUMENTS

| 4,405,531 | 9/1983 | Franz ................................. 260/501.12 |
| 5,188,642 | 2/1993 | Shah et al. ................................. 47/58 |

FOREIGN PATENT DOCUMENTS

| 1 366 379 | 9/1974 | United Kingdom . |
| WO 92/06201 | 4/1992 | WIPO . |

OTHER PUBLICATIONS

STN International, File CAPLUS, CAPLUS accession No. 1978:489564, Lin, Wen–Long et al: "Minimum and zero tillage in paddy rice cultivation", T'ai–wan Nung Yeh Chi K'an (1977), 13(4), 88–96.

Bermer, D.K. et al., "Potential of Imazaquin seed treatment for control of *Striga gesnerioides* and *Alectra vogelii* in Cowpea (*Vigna inguiculata*).", Plant Disease, vol. 8, No. 1, pp. 18–23 (1994).

Bradford, Kent J., "Manipulation of seed water relations via osmotic priming to improve germination under stress conditions.", Hortscience, vol. 21, No. 5, pp. 1105–1112 (1986).

Comai, L. et al., "Expression in plants of a mutant aroA gene from *Salmonella typhimuriom* congers tolerance to glyphosate.", Nature, vol. 317, No. 24, pp. 741–744 (1985).

Foy, Chester L. et al., "Recent approaches for chemical control of broomrape.", Rev. Weed Sci., vol. 4, pp. 123–152 (1989).

Gressel, Jonathan., "The needs for new herbicide–resistant crops.", pp. 283–294 (1992).

Hollander–Czytko, Heike et al., "Glycophosate tolerance of cultured *Corydalis sempervirens* cells is acquired by an increased rate of transcription of 5–enolpruvylshikimate 3–phosphate synthase as well as by a reduced turnover of the enzyme.", Plant Molecular Biology, vol. 20, pp. 1029–1036 (1992).

Joel, Daniel M. et al., "Transgenic crops against parasites.", Nature, vol. 374, pp. 220–221 (1995).

Kishore, G. et al., "5–Enolpyruvylshikimate 3–phosphate synthase.", CHP. 3 Biology for Crop Protection, pp. 37–48 (1988).

(List continued on next page.)

Primary Examiner—S. Mark Clardy
Attorney, Agent, or Firm—Browdy and Neimark

[57] ABSTRACT

Glyphosate salts and mixtures thereof are useful for the preparation of seed dressing, seed priming and seed coating herbicidal compositions for control of parasitic weeds such as Orobanche spp., Cuscuta spp., Striga spp. and Alectra spp., in glyphosate-resistant crop plants, e.g., vegetables, legumes or cereals that contain a gene encoding a modified 5-enolpyruvyl-3-phosphoshikimate (EPSP) synthase and/or produce enhanced amounts of EPSP synthase.

31 Claims, 1 Drawing Sheet

OTHER PUBLICATIONS

WSSA Abstracts, 1995 Meeting of the Weed Science Society of America, vol. 35, (1995), Abstract #15, Ransom et al, "Seed Dressing Maize with Imidazolinone Herbicides...".

Rogers, S.G. et al., "Amplification of the aroA gene from *Escherichia coli* results in tolerance to the herbicide Glyphosate.", Applied and Envir. Microbiology, pp. 37–43 (1983).

Rueppel, Melvin L. et al., "Metabolism and degradation of glyphosate in soil and water.", J. Agric. Food Chem., vol. 25, No. 3, pp. 517–528 (1977).

Scott, James M., "Seed coating and treatments and their effects on plant establishment.", Advances in Agronomy, vol. 42, pp. 42–83 (1989).

Shah, Dilip M., "Engineering herbicide tolerance in transgenic plants.", Science, vol. 233, pp. 478–481 (1986).

Shea, Patrick J. et al., "Reversal of cation–induced reduction in glyphosate activity with EDTA.", Weed Science, vol. 32, pp. 802–806 (1984).

Suh, Hyang et al., "Structure of the amplified 5–enolpyruvylshikimate–3–phosphate synthase gene in glyphosate–resistant carrot cells.", Plant Molecular Biology, vol. 22, pp. 195–205 (1993).

Dawson, Jean H., "Herbicide–treated crop seed.", CHP. 16 Methods of Applying Herbicides, pp. 255–263 (1987).

USE OF GLYPHOSATE SALTS IN SEED DRESSING HERBICIDAL COMPOSITIONS

FIELD OF THE INVENTION

The present invention relates to means and methods for control of parasitic weeds in glyphosate-resistant crop plants, and in particular to the use of glyphosate in seed dressing herbicidal compositions for this purpose.

BACKGROUND OF THE INVENTION

Glyphosate (International Standards Organization common name for the anionic form of N-phosphonomethylglycine) is widely used as a postemergence foliarly applied herbicide.

Until recently glyphosate could only be used to control weeds in a non-selective manner, i.e. if applied to foliage of a standing crop it would kill the crop as well as the weeds. Very low rates of postemergence foliar application of glyphosate have been shown to allow the control of parasitic weeds on standing crops (Foy et al., 1989), but the rate dependence was so crucial and hard to adjust that this use has not been widespread. This use though was predicated on the well known fact that glyphosate is systemic once applied to plant foliage. The ability of glyphosate to act solely through foliage is well accepted in agriculture, as it is well known that it is rapidly degraded in all natural soils, i.e. soils that have not been sterilized (Rueppel et al., 1977). It thus cannot be used as a soil-applied "preemergence" herbicide to control weeds underground, unlike so many commonly used herbicides in agriculture.

As noted above, glyphosate has been used as a non-selective herbicide until recently. That has been changed with the advent of glyphosate-resistant crops. This change has been achieved by engineering a gene coding for enolphosphate shikimate phosphate synthase also known as 5-enolpyruvyl-3-phosphoshikimate (EPSP) synthase, an enzyme that is found in, and is vital to, all plants, and is inhibited by glyphosate. The transgenic plants either contain multiple copies of the natural gene (Rogers et al., 1983) or a modified gene coding for an enzyme that still has a modicum of natural enzyme capacity but is severely reduced in its capacity to bind glyphosate and thus be inhibited (Comai et al., 1985). The gene must code for a modified form of the EPSP synthase, whereby this enzyme is less inhibited by glyphosate than the naturally-occurring enzyme, or for elevated expression of the enzyme, or both.

Such engineered glyphosate-resistant plants often contain subsidiary genetic elements that target the modified gene product to the chloroplasts, and control the level and tissue-localization of the gene (Shah et al., 1986; Kishore, et al., 1988). Examples of such transformed plants are described in U.S. Pat. No. 5,145,783, EP 550633, U.S. Pat. No. 5,310,667 and U.S. Pat. No. 4,971,908, all of them incorporated herein in their entirety by reference. In addition, glyphosate resistance can also be achieved when a plant is able to amplify the gene (Suh et al., 1993) or to enhance the expression of the gene (Hollander-Czytko et al., 1992) coding for EPSP synthase.

Parasitic weeds can either be holoparasites, i.e. plants totally lacking the capacity to produce nutrients for themselves, e.g. Orobanche spp. (common name: broomrapes), or hemiparasites, i.e. they can perform photosynthesis for parts of their life cycles (e.g. Cuscuta spp. (dodders), Striga spp. (witchweeds) and Alectra spp.), but derive much of their organic nutrition, water and minerals from the host plants. The Cuscuta spp. attach to stems and grow above ground, the others attach to roots and spend much of their life cycle below ground until a flower stalk emerges from the soil. One of the major modes of dissemination of parasitic weeds is by contamination of crop seed. Half of the seedlots sampled in local African markets by Bemer et al., 1994 were contaminated with Striga seeds. Orobanche seeds stick to crop seeds and arduous procedures are required to remove them so as not to infest uninfested fields. Thus, a good general topical disinfectant is needed for inactivating parasitic weed seeds in contaminated seedlots prior to sowing. Additionally, there is also a general need for ridding crop seed of other contaminating non-parasitic weed seeds.

Parasitic weeds are a scourge threatening 4% of cropland worldwide, infecting all grains cultivated south of the Sahara (witchweeds=Striga spp) and vegetables, legumes and sunflowers (broomrape=Orobanche spp.) in the Mediterranean, including Israel. The yield loss (on the average) is more than 50% in the infested fields. Till recently there were few selective herbicides capable of controlling the root parasitic weeds while they are still underground, perpetrating their damage.

It has been shown that a foliar application of glyphosate to transgenic plants of the type discussed above allows the systemic inactivation of parasitic weeds (Joel et al., 1995), as had been predicted earlier (Gressel, 1992). It has also been shown that soil-active herbicides at very low rates can be applied to seeds of cow peas, known to be capable of degrading particular soil-active herbicides, in order to control parasitic Striga. Striga has also been controlled at much higher rates in maize with biotechnologically-derived resistance to the same groups of soil-active herbicides (Ransom et al., 1995). Glyphosate is far superior to these other herbicides insofar as weeds are far more prone to evolving resistance to the other herbicides previously used.

None of the prior art publications disclose or suggest the use of the foliar herbicide glyphosate in the soil or for seed dressing.

SUMMARY OF THE INVENTION

It has now been found according to the present invention that glyphosate salts can be used on seeds of glyphosate-resistant crop plants, where the resistance is due to a modified EPSP synthase and/or enhanced amounts of EPSP synthase, in order to protect said crop plants from parasitic weeds.

The present invention thus relates to the use of a glyphosate salt or a mixture thereof for the preparation of a seed dressing herbicidal composition for control of parasitic weeds in glyphosate-resistant crop plants that contain a gene encoding a modified 5-enolpyruvyl-3-phosphoshikimate (EPSP) synthase and/or produce enhanced amounts of EPSP synthase.

In another embodiment, the invention relates to a method for control of parasitic weeds in glyphosate-resistant crop plants that contain a gene encoding a modified EPSP synthase and/or produce enhanced amounts of EPSP synthase, said method comprising application of a herbicidal composition comprising an effective amount of a glyphosate salt or a mixture thereof to seeds of the glyphosate-resistant crop plant prior to planting of said seeds.

In still another embodiment, the invention relates to a method of disinfection of seedlots of glyphosate-resistant crop plants from both parasitic and non-parasitic weed seeds which comprises soaking the seedlots with a composition comprising an effective amount of a glyphosate salt or a mixture thereof.

DETAILED DESCRIPTION OF THE INVENTION

Figure 1:
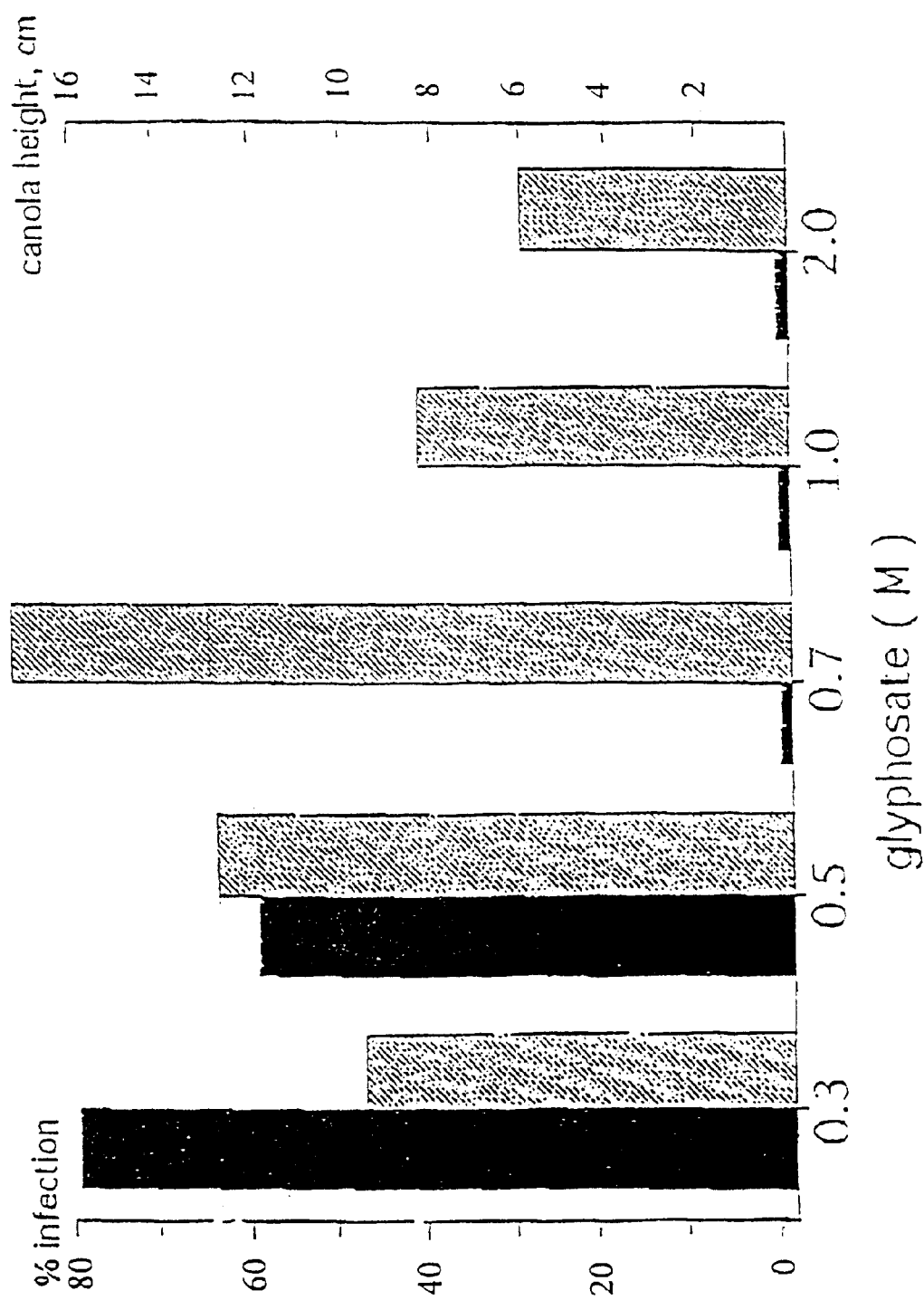
FIG. 1 shows the effect of increasing concentrations of glyphosate isopropylamine salt on infestation of oilseed rape by broomrape (dark bars) and on growth of crop shoots (light bars).

Salts of glyphosate are degraded in soil and have been used only as foliar applied herbicides. They lacked selectivity with crops until the advent of glyphosate-resistant plants. According to the invention, a novel seed dressing technology is disclosed for treating glyphosate-resistant crops to simultaneously rid the crop seed of contaminating weed seed prior to planting, while providing future immunity to the crop from infection by parasitic weeds residing in the soil.

The present invention thus relates to a novel means for disinfecting certain crop plant seeds from contaminating weed seeds as well as for protecting crop plants from infection by parasitic weed seed that contaminates the soil.

According to the invention, herbicidal compositions for seed dressing are provided comprising a glyphosate salt or a mixture thereof in a predominantly aqueous solution.

The compositions of the invention are very useful in disinfecting specific crop seed of parasitic and normal weed seeds. As described in the examples herein, glyphosate can be "primed" in crop seeds by soaking glyphosate-resistant crop seeds with exceedingly high concentrations of glyphosate. The invention also encompasses seed priming and seed coating by using technologies well-known in the art for seed priming (Bradford, 1986) and seed coating (Scott, 1989) with vitamins and nutrients as well as microorganisms.

The compositions of the invention comprise a soluble form of glyphosate, i.e. a salt or other derivative. Many such salts are known, as for example those disclosed in U.S. Pat. No. 4,405,531 and in Israeli Patent No. 37993, both patents being herein incorporated by reference. Examples of such salts include, but are not limited to, inorganic salts such as salts of alkali metals, e.g. sodium, potassium, lithium, cesium and rubidium; alkaline earth metals, e.g. magnesium, calcium, barium, strontium and beryllium; iron, manganese, zinc, copper, nickel and amronium, as well as organic salts such as those derived from primary, secondary, tertiary and heterocyclic amines. The amines may be aliphatic such as $C_1$–$C_{20}$ mono-, di- and tri-alkyl, -hydroxyalkyl and -alkenyl monoamines or diarnines, e.g. methylamine, ethylamine, n-propylamine, isopropylamine, n-butylamine, isobutylamine, sec-butylamine, n-amylamine, isoamylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, nonadecylamine, eicosylamine, dimethylamine, methylethylamine, diethylamine, methylisopropylamine, ethylisopropylamine, di-n-propylamine, diisopropylamine, methybutylamine, methylhexylamine, ethylbutylamine, trimethylamine, triethylamine, tri-n-propylamine, triisopropylamine, tri-n-butylamine, tri-sec-butylamine, triisobutylamine, hydroxyethylamine, di(hydroxyethyl) amine, hydroxy-n-propylamine, hydroxyisopropyl-amine, allylamine, n-butenyl-2-amine, n-pentenyl-2-amine, ethylenediamine and propylenediamine, or aromatic amines, e.g. aniline, methoxyaniline, ethoxyaniline, o,m,p-toluidine, phenylenediarnine, benzidine, naphthylarnine, or heterocyclic amines, e.g. pyrrolidine, piperidine, pyridine, morpholine, indoline. azepine, and thiamine.

The most active glyphosate salts have as counter ions monovalent metal cations, $NH_4^+$, cationic detergents, or organic cations, such as organic amines. The mostly widely counter ion used to solubilize glyphosate in water in agricultural use is isopropylamine, and constitutes a preferred embodiment of the invention.

Some inorganic divalent and trivalent metal cations known to precipitate or otherwise inactivate glyphosate, e.g. Ca, Mg, Fe, can also be used according to the invention when applied together with a chelating agent of stronger binding capacity than the weak binding capacity of glyphosate, e.g. EDTA (ethylene diamine tetraacetic acid) (Shea and Tupy, 1984). Thus, such compounds, commonly used in agriculture to stabilize iron ions from precipitating, may possibly be added to a priming solution of the invention.

A mixture of counter ions can be used as fertilizer to support growth of the crop seeds (e.g. $K^+$, $NH_4^+$) along with $Na^+$, organic amine cations, or small amounts of a cationic detergent to lower the surface tension of the mixture around both the crop seeds and the contaminating parasite seeds. A non-ionic detergent in small amounts can also be used for the latter purpose.

The type of glyphosate salts, duration of soaking, and concentration of glyphosate appropriate for charging the crop seed with sufficient glyphosate to systemically disinfect the crop from attacking parasite as well as to disinfect seed batches from parasite and normal weed seeds, will be dependent on the crop species as each crop species has seed with different properties. The conditions required are determined by seed priming technologies well-known in the art. Similarly, seed can be sown wet, partially dried or redried, again as determined for different crops and cropping systems along well developed lines for seed priming and vernalization that can be readily determined from the teaching of this specification, including examples, by one skilled in the art.

The term "dressing" is used here to denote all treatments of seeds including "coating", i.e. external covering of the seeds, and "priming", i.e. treatments whereby the seed is soaked in a solution. Seeds can be planted wet after priming or can be re-dried, as used herein.

The term "disinfectant" is used here for materials that render normal or parasitic weed seeds inactive or for a compound that systematically stops or suppresses the growth of a parasitic weed before or after it attaches to the crop. The term "parasitic weed" is used for members of several genera of weeds: e.g. Orobanche, Striga, Cuscuta, Alectra, which germinate and then attach to root, stems or leaves of plants. "Crop" is used herein for any plant species cultivated by man for economic or esthetic reasons, whether for food, fiber, decoration, medicines, or otherwise, preferably vegetables, legumes and cereals. "Normal" weeds are used herein to distinguish from parasitic weeds. "Systemic disinfectant" is used for a disinfectant that moves within crop tissues to the organ attacked by the parasite, moving to the parasite from within the plant tissues.

The composition for seed dressing used according to the invention will comprise about 0.3–2M, preferably 0.6–0.8M, of an active glyphosate salt. Very good results of control of broomrapes with little effect on the crop were achieved according to the invention with e.g. 0.7M glyphosate salt (see FIG. 1), a concentration much higher than the range usually employed with soil-active herbicides when the herbicide is applied directly to the soil. In the priming method, the herbicide is localized and thus less herbicide per hectare is used.

Thus according to the invention, seed treatment and priming of transgenic, target site glyphosate-resistant crop plants can be achieved with active salts of glyphosate or mixtures thereof or with other seed-priming compounds to control all parasitic weeds attacking these crops and for disinfecting such crop seeds from contaminating parasitic and normal weed seeds.

The concentration of the glyphosate composition and the time of seed priming or soaking will vary according to the plant species. The soaking time is usually in the range to of 30 min to 8 hours, preferably 2–4 hours.

The invention will now be illustrated by the following non-limiting examples.

EXAMPLES

Example 1

Formulated glyphosate (Roundup™, Monsanto, isopropylamine salt in solution with detergent) was brought to 1.0 M. Seed of transgenic oilseed rape (*Brassica napus*) bearing a modified EPSP synthase was soaked in solutions of various concentrations of the glyphosate salt for four hours and then planted in pots containing 10 mg seeds/kg soil of the root infecting parasitic weed *Orobanche aegyptiaca* (Egyptian broomrape). The results are illustrated in FIG. 1. From the data, it is apparent that rates lower than 0.7 M of this formulation (at this duration of soaking) did not protect against the parasite. The rate of 0.7 M gave maximum growth of the crop with total disinfection of broomrape, as ascertained both by counting emerging stalks of the parasite and by removing adhering soil and viewing the roots. 1 M glyphosate also caused some reduction of crop growth, possibly due to toxicity from the isopropylamine counter ion or from the detergent.

Example 2

A solution of the formulated isopropylarnine salt was prepared as in Example 1 or the potassium glyphosate salt was prepared by titrating a suspension of glyphosate acid to a neutral pH 7 solution with KOH. Seeds of two weey grasses (*Avena sterilis* and *Phalaris minor*) and two small-seed broad leaf weeds (*Stellaria media* and Amaranthus sp.) and one larger seeded broadleaf weed (*Sinapis arvensis*) were soaked in glyphosate salt. Parallel seed of all species was soaked in water for same duration of time. The seeds were planted in soil and observed. From the results in Table 1 it is clear that glyphosate effectively inactivated weed seeds by a treatment that did not affect the glyphosate-resistant crop.

TABLE 1

Toxicity of glyphosate to weed seeds following soaking

| M glyphosate | duration of soaking(h) | weed species | symptoms on treated weeds[b] |
|---|---|---|---|
| 0.7 IPA[a] | 4 | Avena sterilis | no emergence |
| 0.7 IPA | 4 | Phalaris minor | emergence, chlorosis, death |
| 0.7 IPA | 4 | Amaranthus sp. | emergence, chlorosis, death |

TABLE 1-continued

Toxicity of glyphosate to weed seeds following soaking

| M glyphosate | duration of soaking(h) | weed species | symptoms on treated weeds[b] |
|---|---|---|---|
| 0.67 K | 2 | Sinapis arvensis | no emergence |
| 0.67 K | 2 | Stellaria media | emergence, chlorosis, death | a. IPA - isopropylamine salt, formulated with detergent: K - potassium salt without detergent
b. All weed species mock treated (soaked in water for same duration) seeds germinated normally. Some of the treated weed species failed to emerge from the soil, others emerged, became stunted and chlorotic and then died.

Example 3

A neutral glyphosate salt solution is prepared as described in Example 2 and seeds of the parasitic weed, e.g. *Orobanche aegyptiaca*, are soaked in various concentrations of the glyphosate salt for 4 h. The germination stimulator GR 47 is added at a standard concentration and time to cause rapid and uniform germination of the parasite seeds. The seeds are sedimented by centrifugation and suspended in water and immediately planted on a medium typically used to check Orobanche seed viability.

Although the invention is described with respect to a specific salt, the details hereof are not to be construed as limitations except to the extent indicated in the following claims.

REFERENCES

1. Berner, D. K., Cardwell, K. F., Faturoti, B. O., Ikie, F. O., and Williams, O. A. (1994) Relative roles of wind, crop seeds, and cattle in the dispersal of Striga species. Plant Disease 78: 402–406.
2. Bradford, K. J. (1986) Manipulation of seed water relations via osmotic priming to improve germination under stress conditions. HortScience 2:1105–1112.
3. Comai, L., Faccioti, D., Hiatt, W. R., Thompson, G., Rose, R. E. and Stalker, D. M. (1985) Expression in plants of a mutant aroA gene from *Salmonella typhimurium* confers tolerance to glyphosate. Nature 317: 741–744.
4. Foy, C. L., Jain, R. and Jacobsohn, R. (1989) Recent approaches for chemical control of broomrape (Orobanche spp. ) Rev. Weed Sci. 4:123–152.
5. Gressel, J. (1992) The need for new herbicide-resistant crops. In Denholm, A., A. L. Devonshire, D. W. Hollomon (eds), Achievements and developments in combating pesticide resistance. (London: Elsevier), pp. 283–294.
6. Hollander-Czytko, H; Sommer, I and Amrhein, N (1992) Glyphosate tolerance of cultured *Corydalis sempervirens* cells is acquired by an increased rate of transcription of EPSP—synthase as well as by reduced enzyme turnover. Plant Molecular Biology 20: 1029–1036.
7. Joel, D. M., Kleifeld, Y., Losner-Goshen, D., Herzlinger, G. and Gressel, J. (1995) Transgenic crops against parasites. Nature 374, 220–221.
8. Kishore, G., Shah, D., Padgette, S., della-Cioppa, G., Gasser, C., Re, D., Hironaka, C. Taylor, M., Wibbenmneyer, J., Eichholtz. D., Hayford, M., Hoffman, N., Delannay, X., Horsch, R., Klee, H., Rogers, S., Rochester, D., Brundage, L., Sanders, P. and Fraley, R. T., (1988) 5-Enolpyruvylshikimate 3-phosphate synthase: from biochemistry to genetic engineering of glyphosate tolerance. Biotechnology for Crop Protection (Hedin, P. A., erenn, J. J. and Hollingworth, R. M. eds.) Am. Chem. Soc. Symp. Ser Washington DC, 379:37–48.

9. Ransom, J. K., Odhiambo, G. D., Kisumu, K. and Gressel, J., (1995). Seed dressing maize with imidazolinone herbicides to control *Striga hermonthica* (Del.) Benth. Weed Science Society American Abstracts 35, 15.

10. Rogers, S. G., Brand, L. A., Holder, S. B., Sharp, E. S. and Brackin, M. J. (1983) Amplification of the aroA gene from *E. coli* results in tolerance to the herbicide glyphosate. Appl. Environ. Microbiol. 46:37–43.

11. Rueppel, M. L., Brightwell, B. B., Schaefer, J. and Marvel, J. T. (1977) Metabolism and degradation of glyphosate in soil and water. J. Agric. Food Chem. 25: 517–528.

12. Scott, J. (1989) Seed coatings and treatments and their effects on plant establishment. Adv. in Agron. 42:43–83.

13. Shah, D. M., Horsch, R. B., Klee, H. J., Kishore, G. M., Winter, J. A., Turner, N. E., Hironaka, C. M., Sanders, P. R., Gasser, C. S., Aykent, S., Siegel, N. R., Rogers, S. G. and Fraley R. T. (1986) Engineering herbicide tolerance in transgenic plants. Science 233:478–481.

14. Shea, P. J. and Tupy, D. R. (1984) Reversal of cation-induced reduction in glyphosate activity with EDTA. Weed Science 32: 802–806.

15. Suh, H; Hepburn, A G; Kriz, A L and Widholm, J M (1993) Structure of the amplified EPSP—synthase gene in glyphosate-resistant carrot cells. Plant Molecular Biology 22 :195–205.

What is claimed is:

1. A seed of a glyphosate-resistant crop plant that contains a gene encoding a modified 5-enolpyruvyl-3-phosphoshikimate (EPSP) synthase and/or produce enhanced amount of EPSP synthase, which seed has been primed with a glyphosate salt or a mixture thereof.

2. A seed in accordance with claim 1, wherein said seed has been primed by soaking the seed with a predominantly aqueous composition of a glyphosate salt or a mixture thereof for a period of time sufficient to protect the plants growing from said seeds from infection by parasitic seeds residing in the soil.

3. A seed in accordance with claim 1, wherein the glyphosate salt is an inorganic salt selected from the group consisting of salts of alkali metals, alkaline earth metals, manganese, copper, zinc, iron, nickel and ammonium.

4. A seed according to claim 1, wherein the glyphosate salt is an organic salt of an aliphatic mono-, di- or tri-alkylamine, -hydroxyalkylamine or -alkenyl-amine, an aromatic amine or a heterocyclic amine.

5. A seed in accordance with claim 1 which is a seed of a vegetable, legume or cereal.

6. A seedlot comprising predominantly seeds of a glyphosate-resistant crop plant that contain a gene encoding a modified 5-enolpyruvyl-e-phosphoshikimate (EPSP) synthase and/or produce enhanced amounts of EPSP synthase, and a contaminating amount of weed seeds, which seedlot has been primed by soaking the seedlot in a predominantly aqueous composition of a glyphosate salt or a mixture thereof for a period of time sufficient to prevent infection of the crop plants growing from the crop seeds of the seedlot, by weeds which might otherwise have grown from the weed seeds which contaminate the seedlot.

7. A seedlot in accordance with claim 6, wherein the glyphosate salt is an inorganic salt selected from the group consisting of salts of alkali metals, alkaline earth metals, manganese, copper, zinc, iron, nickel and ammonium.

8. A seedlot in accordance with claim 6, wherein the glyphosate salt is an organic salt of an aliphatic mono-, di- or tri-alkylamine, -hydroxyalkylamine or -alkenyl-amine, an aromatic amine or a heterocyclic amine.

9. A seedlot in accordance with claim 6, wherein the contaminating weed seeds are parasitic or normal weed seeds.

10. A method for control of parasitic weeds in glyphosate-resistant crop plants that contain a gene encoding a modified 5-enolpyruvyl-3-phosphoshikimate (EPSP) synthase and/or produce enhanced amounts of EPSP synthase, said method comprising priming seeds of glyphosate-resistant crop plants, prior to planting of said seeds, with a herbicidal composition comprising an effective amount of a glyphosate salt or a mixture thereof.

11. A method according to claim 10, wherein said priming comprises soaking the seeds with a predominantly aqueous composition of a glyphosate salt or a mixture thereof for a period of time sufficient to protect the plants growing from said seeds from infection by parasitic seeds residing in the soil.

12. A method according to claim 10, wherein the composition comprises 0.3–2 M of the glyphosate salt.

13. A method according to claim 12 wherein the composition comprises 0.6–0.8 M of the glyphosate salt.

14. A method according to claim 10, wherein the seeds are primed for 30 minutes to 8 hours.

15. A method according to claim 10, for control of parasitic weeds selected from the consisting of Orobanche spp., Cuscufa spp., Striga spp. and Alectra spp.

16. A method according to claim 10, wherein the crop plants are vegetables, legumes or cereals.

17. A method according to claim 10, wherein the glyphosate salt is an inorganic salt selected from the group consisting of salts of alkali metals, alkaline earth metals, manganese, copper, zinc, iron, nickel and ammonium.

18. A method according to claim 17, wherein the glyphosate salt is the potassium salt.

19. A method according to claim 10, wherein the glyphosate salt is an organic salt of an aliphatic mono-, di- or tri-alkylamine, -hydroxyalkylamine or -alkenyl-amine, an aromatic amine or a heterocyclic amine.

20. A method according to claim 19, wherein the glyphosate salt is the isopropylamine glyphosate salt.

21. A method in accordance with claim 10, wherein the seeds are primed for 2–4 hours.

22. A method of disinfection of seedlots of glyphosate-resistant crop plants that contain a gene encoding a modified 5-enolpyruvyl-3-phosphoshikimate (EPSP) synthase and/or produce enhanced amounts of EPSP synthase, from contaminating parasitic and normal weed seeds, which comprises priming said seedlots, prior to planting, with a composition comprising an effective amount of a glyphosate salt or a mixture thereof.

23. A method according to claim 22, wherein the glyphosate salt is an inorganic salt selected from the group consisting of salts of alkali metals, alkaline earth metals, manganese, copper, zinc, iron, nickel and ammonium.

24. A method according to claim 23, wherein the glyphosate salt is the potassium salt.

25. A method according to claim 22, wherein the glyphosate salt is an organic salt of an aliphatic mono-, di- or tri-alkylamine, -hydroxyalkylamine or -alkenyl-amine, an aromatic amine or a heterocyclic amine.

26. A method according to claim 25, wherein the glyphosate salt is the isopropylamine glyphosate salt.

27. A method according to claim 22, wherein the composition is a predominantly aqueous composition comprising 0. 3–2 M of the glyphosate salt.

28. A method according to claim 27, wherein the aqueous composition comprises 0.6–0.8 M of the glyphosate salt.

29. A method according to claim 24, wherein said priming comprises soaking the seedlot in a predominantly aqueous composition of a glyphosate salt or a mixture thereof for a period of time sufficient to prevent infection of the crop plants growing from the crop seeds of the seedlot, by weeds which might otherwise have grown from the weed seeds which contaminate the seedlot.

30. A method according to claim 24, wherein the seeds are primed for 30 minutes to 8 hours.

31. A method according to claim 24, wherein the contaminating weed seeds are parasitic or normal weed seeds.

* * * * *